United States Patent [19]

Chakrabarti et al.

[11] Patent Number: 5,627,178

[45] Date of Patent: *May 6, 1997

[54] 2-METHYL-THIENO-BENZODIAZEPINE

[75] Inventors: Jiban K. Chakrabarti, Camberley; Terrence M. Hotten, Hants; David E. Tupper, Reading, all of England

[73] Assignee: Lilly Industries Limited, Basingstoke, England

[*] Notice: The term of this patent shall not extend beyond the expiration date of Pat. No. 5,229,382.

[21] Appl. No.: 387,997

[22] Filed: Feb. 13, 1995

Related U.S. Application Data

[63] Continuation-in-part of Ser. No. 44,844, Apr. 8, 1993, abandoned, which is a continuation-in-part of Ser. No. 890,348, May 22, 1992, Pat. No. 5,229,382, which is a continuation of Ser. No. 690,143, Apr. 23, 1991, abandoned.

[51] Int. Cl.$^6$ .................................................. A61K 31/55
[52] U.S. Cl. ........................................................ 514/220
[58] Field of Search .............................................. 514/220

[56] References Cited

U.S. PATENT DOCUMENTS

| | | | |
|---|---|---|---|
| 4,115,568 | 9/1978 | Chakrabarti et al. | 424/250 |
| 4,115,574 | 9/1978 | Chakrabarti et al. | 424/250 |
| 5,229,382 | 7/1993 | Chakrabarti et al. | 514/220 |

OTHER PUBLICATIONS

N. A. Moore et al., *Journal of Pharmacology & Experimental Therapeutics*, 262:2, pp. 545–551 (1992).

J. K. Chakrabarti et al., *J. Med. Chem.*, 23, pp. 878–884, (1980).

N. C. Tye et al., Second International Conference on Schizophrenia, Vancouver, B.C., Jul. 19–22, 1992.

C. M. Beasley, Jr. et al., Second International Conference on Schizophrenia, Vancouver, B.C., Jul. 19–22, 1992.

R. W. Fuller, et al., *Research Communications in Chemical Pathology and Pharmacology*, 77:1 pp. 87–93 (1992).

N. A. Moore, et al., *Curr. Opin. Invest. Drugs*, 2:4 pp. 281–293, (1993).

*Primary Examiner*—Philip I. Datlow
*Attorney, Agent, or Firm*—MaCharri Vorndran-Jones; David E. Boone

[57] ABSTRACT

2-Methyl-4-(4-methyl-1-piperazinyl)-10H-thieno-[2,3-b][1,5]benzodiazepine, or an acid salt thereof, has pharmaceutical properties, and is of particular use in the treatment of disorders of the central nervous system. The compound has the following structure:

10 Claims, No Drawings

2-METHYL-THIENO-BENZODIAZEPINE

CROSS-REFERENCE

This application is a continuation-in-part of application Ser. No. 08/044,844, filed Apr. 8, 1993, now abandoned which was a continuation-in-part of application Ser. No. 07/890,348, filed May 22, 1992, now U.S. Pat. No. 5,229,382 which was a continuation of Ser. No. 07/690,143, filed Apr. 23, 1991 now abandoned.

This invention relates to novel organic compounds and the use thereof as pharmaceuticals.

Currently there are many drugs available for the treatment of disorders of the central nervous system. Amongst these drugs is a category known as antipsychotics for treating serious mental conditions such as psychosis, including but not limited to schizophrenia and schizophreniform illnesses. The skilled artisan will recognize that these psychotic conditions are characterized by hallucinations, delusions, or grossly disorganized behavior which indicate that the patient suffers from gross impairment in reality testing. Drugs having said antipsychotic activity can be useful for treating a variety of important psychotic disorders. The drugs available for such conditions are often associated with undesirable side effects, and there is a need for better products that control or eliminate the symptoms in a safer and more effective way. Furthermore, many patients do not respond or only partially respond to present drug treatment, and estimates of such partial- or non-responders vary between 40% and 80% of those treated.

Ever since antipsychotics were introduced it has been observed that patients are liable to suffer from drug-induced extrapyramidal symptoms which include drug-induced Parkinsonism, acute dystonic reactions, akathisia, tardive dyskinesia and tardive dystonia. The Simpson Angus Scale, Barnes Akathisia Rating Scale and Abnormal Involuntary Movement Scale (AIMS) are well known scales for assessing extrapyramidal symptoms. The great majority of drugs available for treatment of schizophrenia are prone to produce these extrapyramidal side effects when used at dosages that yield a beneficial effect on the symptoms of the disease. The severity of adverse events and/or lack of efficacy in a considerable number of patients frequently results in poor compliance or termination of treatment.

Many of the drugs are associated with a sedative effect and may also have an undesirable influence on the affective symptoms of the disease, causing depression. In some instances long term use of the drug leads to irreversible conditions, such as the tardive dyskinesia and tardive dystonia referred to supra.

A widely-used antipsychotic, haloperidol, is one such drug, which has been reported as causing a high incidence of extrapyramidal symptoms and may also cause tardive dyskinesia. More recently, clozapine, one of a large group of heterocyclic antipsychotics, has been introduced with the claim that it is free from extrapyramidal effects. However, the compound was found to cause agranulocytosis in some patients, a condition resulting in a lowered white blood cell count which can be life-threatening, and it may now only be employed under very strict medical observation and supervision.

A further group of antipsychotic compounds is that described in British Patent 1 533 235. These include thieno-benzodiazepines having the following structural nucleus.

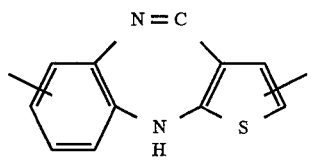

The lead compound from this group, flumezapine, (7-fluoro-2-methyl-10-(4-methyl-1-piperazinyl)-4H-thieno [2,3-b][1,5]-benzodiazepine), was developed to the stage of being clinically administered to psychiatric patients suffering from schizophrenia. A total of 17 patients received treatment with flumezapine before the clinical trial was terminated after consultation with the U.S. Food and Drug Administration, because of an unacceptably high incidence of raised enzyme levels in the treated patients. The enzyme, creatinine phosphokinase (CPK), and the liver enzymes, serum glutamate oxalacetic transaminase (SGOT) and serum glutamate pyruvate transaminase (SGPT), estimated from blood samples taken from patients, were in substantial excess of normal values, indicating the possibility of toxicity. In respect of its tendency to raise liver enzyme levels, flumezapine is similar to chlorpromazine, an antipsychotic which has long been in use but whose safety has been called into question.

In clinical trials with flumezapine two of the patients showed the emergence of extrapyramidal side effects as measured on the AIMS scale referred to above.

We have now discovered a compound which possesses surprising and unexpected properties by comparison with flumezapine and other related compounds.

The 2-methyl-4-(4-methyl-1-piperazinyl)-10H-thieno[2,3-b][1,5]benzodiazepine compound is of the formula

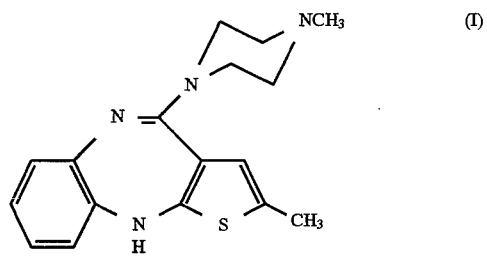

or an acid addition salt thereof. The free base of formula (I) is 2-methyl-4-(4-methyl-1-piperazinyl)-10H-thieno[2,3-b][1,5]benzodiazepine.

The 2-methyl-4-(4-methyl-1-piperazinyl)-10H-thieno[2,3-b][1,5]benzodiazepine compound has given surprising and excellent results, described in greater detail below, in experimental screens for testing activity on the central nervous system and in clinical trials, which results suggest its usefulness for the relatively safe and effective treatment of a wide range of disorders of the central nervous system.

The results of pharmacological tests show that 2-methyl-4-(4-methyl-1-piperazinyl)-10H-thieno[2,3-b][1,5]benzodiazepine is an antagonist of dopamine at D-1 and D-2 receptors, and in addition has antimuscarinic anticholinergic properties and antagonist activity at 5HT-2 receptor sites. It also has antagonist activity at noradrenergic α-receptors. These properties indicate that the compound is a potential neuroleptic with relaxant, anxiolytic and anti-emetic properties, and may be useful in treating psychotic conditions such as, but not limited to, schizophrenia, schizophreniform diseases and mania. At lower doses the compound is indicated for use in the treatment of mild anxiety states. The properties of 2-methyl-4-(4-methyl-1-piperazinyl)-10H-thieno[2,3-b][1,5]benzodiazepine suggest that it would be useful in the treatment of any pathologic psychologic condition, where delusions, hallucinations, disorganized behavior, or anxiety are consistent with manifestation of that pathologic condition.

Pathologic psychological conditions which are psychoses or may be associated with psychotic features include, but are not limited to the following disorders which have been characterized in the DSM-III-R. *Diagnostic and Statistical Manual of Mental Disorders, Revised*, 3rd Ed. (1980). The DSM-III-R was prepared by the Task Force on Nomenclature and Statistics of the American Psychiatric Association, and provides clear descriptions of diagnostic catagories. The numbers in parenthesis refer to the DSM-III-R categories. The skilled artisan will recognize that there are alternative nomenclatures, nosologies, and classification systems for pathologic psychological conditions and that these systems evolve with medical scientific progress.

Examples of pathologic psychologic conditions which may be treated using 2-methyl-4-(4-methyl-1-piperazinyl)-10H-thieno[2,3-b][1,5]benzodiazepine include, but are not limited to, Moderate Mental Retardation (318.00), Severe Mental Retardation (318.10), Profound Mental Retardation (318.20), Unspecified Mental Retardation (319.00), Autistic disorder (299.00), Pervasive Development Disorder NOS (299.80), Attention-deficit Hyperactivity Disorder (314.01), Conduct Disorder, Group Type (312.20), Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Primary Degenerative Dementia of the Alzheimer Type, Senile Onset, with Delirium (290.30), Primary Degenerative Dementia of the Alzheimer Type, Senile Onset, with Delusions (290.20), Primary Degenerative Dementia of the Alzheimer Type, Senile Onset, with Depression (290.21), Primary Degenerative Dementia of the Alzheimer Type, Senile Onset, Uncomplicated (290.00), Primary Degenerative Dementia of the Alzheimer Type, Presenile Onset, with Delirium (290.11), Primary Degenerative Dementia of the Alzheimer Type, Presenile Onset, with Delusions (290.12), Primary Degenerative Dementia of the Alzheimer Type, Presenile Onset, with Depression (290.13), Primary Degenerative Dementia of the Alzheimer Type, Presenile Onset, Uncomplicated (290.10), Multi-infarct dementia, with Delirium (290.41), Multi-infarct dementia, with Delusions (290.42), Multi-infarct dementia, with Depression (290.43), Multi-infarct dementia, Uncomplicated (290.40), Senile Dementia NOS (290.00), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Personality Disorder (310.10), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorgahized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), Induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Major Depression, Single Episode, Severe, without Psychotic Features (296.23), Major Depression, Recurrent, Severe, without Psychotic Features (296.33), Bipolar Disorder, Mixed, with Psychotic Features (296.64), Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), Major Depression, Recurrent with Psychotic Features (296.34) Personality Disorders, Paranoid (301.00), Personality Disorders, Schizoid (301.20), Personality Disorders, Schizotypal (301.22), Personality Disorders, Antisocial (301.70), and Personality Disorders, Borderline (301.83).

Preferably, an effective amount of -2-methyl-4-(4-methyl-1-piperazinyl)-10H-thieno-[2,3-b][1,5]benzodiazepine, or an acid addition salt thereof, is used for the treatment of Moderate Mental Retardation; Severe Mental Retardation; Profound Mental Retardation; Autistic disorder; Pervasive Development Disorder NOS; Conduct Disorder, Group Type; Conduct Disorder, Solitary Aggressive Type; Tourette's Disorder; Primary Degenerative Dementia of the Alzheimer Type, Senile Onset, with Delirium; Primary Degenerative Dementia of the Alzheimer Type, Senile Onset, with Delusions; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Personality Disorders, Paranoid; Personality Disorders, Schizoid; Personality Disorders, Schizotypal; Personality Disorders, Antisocial; Personality Disorders, Borderline; Hebephrenic Schizophrenia; Post-Schizophrenic Depression; Delusional Disorder; and Other Persistent Delusional Disorders.

More preferredly, 2-methyl-4-(4-methyl-1-piperazinyl)-10H-thieno-[2,3-b]-[1,5]benzodiazepine is used to treat the following pathologic psychological conditions including Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Examples of conditions which are most preferredly treated using 2-methyl-4-(4-methyl-1-piperazinyl)-10H-thieno-[2,3-b][1,5]benzodiazepine include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Personality Disorders, Schizoid; Personality Disorders, Schizotypal; Hebephrenic Schizophrenia; and Post-Schizophrenic Depression.

Examples of anxiety disorders which may more preferredly be treated using an effective amount of 2-methyl-4-(4-methyl-1-piperazinyl)-10H-thieno[2,3-b][1,5]benzodiazepine, or an acid addition salt thereof, include Psychoactive Substance Anxiety Disorder; Organic Anxiety Disorder; Obsessive Compulsive Disorder; Post-traumatic Stress Disorder; Generalized Anxiety Disorder; and Anxiety Disorder NOS.

Examples of the anxiety disorders which are most preferredly treated using 2-methyl-4-(4-methyl-1-piperazinyl)-10H-thieno-[2,3-b][1,5]benzodiazepine include Organic Anxiety Disorder; Obsessive Compulsive Disorder; Post-traumatic Stress Disorder; Generalized Anxiety Disorder; and Anxiety Disorder NOS.

As mentioned above, 2-methyl-4-(4-methyl-1-piperazinyl)-10H-thieno[2,3-b][1,5]benzodiazepine has shown a high level of activity in the clinical evaluation of psychiatric patients suffering from schizophrenia, and it exhibits this high activity at surprisingly low dosage levels. The dosage levels have been found to be lower than would be expected from observations of the compound made in initial tests on animal models. Its response profile in patients follows that of known antipsychotic agents when they have been used successfully, there being a clear similarity between the performance of the compound and that of known antipsychotic agents in its ratings on the major assessment scales such as Brief Psychiatric Rating Scale (BPRS), and Clinical Global Impression (CGI).

In the first completed open (as opposed to blind) study of 2-methyl-4-(4-methyl-1-piperazinyl)-10H-thieno[2,3-b][1,5]benzodiazepine in schizophrenic patients, six out of eight patients who completed at least 2 weeks of treatment showed between 66% and 87% improvement at 4 weeks, as assessed on BPRS scale, at daily dosages between 5 and 30 mg. Preliminary results from a further three ongoing clinical trials now appear to confirm this high level of efficacy and at doses lower than or at the low end of the dosage level used in the first study, for example, at 2.5 and 5 mg per day.

Moreover, although some patients have exhibited increases in hepatic enzyme levels, no patient treated to date has experienced clinically significant hepatic disease. Plasma levels of creatinine phosphokinase (CPK) are lower than with flumezapine, indicating a lower adverse effect on muscular tissue. Furthermore, 2-methyl-4-(4-methyl-1-piperazinyl)-10H-thieno[2,3-b][1,5]benzodiazepine causes lower elevation of prolactin levels than other currently used neuroleptic drugs and this suggests fewer disturbances of the menstrual cycle, and less gynecomastia and galactorrhea. No substantial clinically significant alteration of white blood cell count has been observed in clinical studies.

In dog toxicity studies with a closely analogous compound, 2-methyl-4-(4-methyl-1-piperazinyl)-10H-thieno[2,3-b][1,5]benzodiazepine, at a dosage of 8 mg/kg, it was observed that four out of eight dogs showed a significant rise in cholesterol levels, whereas 2-methyl-4-(4-methyl-1-piperazinyl)-10H-thieno[2,3-b][1,5]benzodiazepine did not show any rise in cholesterol levels.

Overall, therefore, in clinical situations, 2-methyl-4-(4-methyl-1-piperazinyl)-10H-thieno[2,3-b][1,5]benzodiazepine shows marked superiority, and a better side effects profile than prior known antipsychotic agents, and has a highly advantageous activity level.

The compound 2-methyl-4-(4-methyl-1-piperazinyl)-10H-thieno[2,3-b][1,5]benzodiazepine can be used both in its free base and acid addition salt forms. The acid addition salts are preferably the pharmaceutically acceptable, non-toxic addition salts with suitable acids, such as those of inorganic acids, for example hydrochloric, hydrobromic, nitric, sulphuric or phosphoric acids, or of organic acids, such as organic carboxylic acids, for example glycollic, maleic, hydroxymaleic, fumaric, malic, tartaric, citric or lactic acid, or organic sulphonic acids for example methane sulphonic, ethane sulphonic, 2-hydroxyethane sulphonic, toluene-p-sulphonic or naphthalene-2-sulphonic acid. In addition to pharmaceutically acceptable acid addition salts, other acid addition salts are included in the invention, for example, those with picric or oxalic acid, since they have potential to serve as intermediates in purification or in the preparation of other, for example, pharmaceutically acceptable, acid addition salts, or are useful for identification, characterization or purification of the free base.

According to a further aspect of the invention there is provided a process for producing a compound of formula (I) or an acid addition salt thereof, which comprises (a) reacting N-methylpiperazine with a compound of the formula

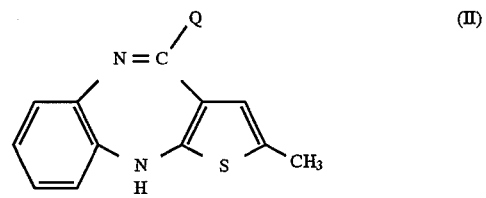 (II)

in which Q is a radical capable of being split off, or (b) ring-closing a compound of the formula

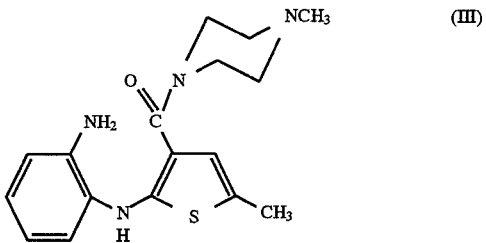 (III)

Appropriate reaction conditions and suitable values of Q can readily be chosen for these processes.

In reaction (a) the radical Q can, for example, be an amino group or a mono- or dialkyl-substituted amino group (each alkyl substituent suitably containing 1 to 4 carbon atoms), hydroxyl, thiol, or an alkoxy, alkylthio or alkylsulphonyl group suitably containing 1 to 4 carbon atoms, for example a methoxy or methylthio group, or a halogen atom, especially a chlorine atom. Preferably, Q is amino (—NH₂), hydroxyl or thiol, and amino is most preferred. The reaction is preferably carried out at a temperature of from 50° C. to 200° C.

When Q is amino, the intermediate of formula (II) may also exist in the imino form:

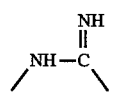

and when Q is hydroxyl or thiol, the intermediates of formula (II) may exist in their amide and thioamide forms:

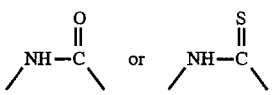

The amidine of formula (II) (Q is —NH₂), can be in salt form, for example a salt of a mineral acid such as the hydrochloride, and can be reacted with N-methylpiperazine in an organic solvent such as anisole, toluene, dimethylformamide or dimethyl-sulphoxide, preferably at a temperature range of 100° to 150° C.

The amidine is prepared by condensing a thiophene compound of formula

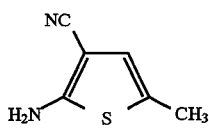

with an ortho-halonitrobenzene, in the presence of a base, for example sodium hydride, in a solvent such as tetrahydrofuran or n-butyl lithium in tetrahydrofuran, or potassium carbonate or lithium hydroxide in dimethylsulphoxide or aqueous sodium hydroxide in dimethylsulfoxide, or with a tetraalkyl-ammonium salt in a two-phase system, to form a nitronitrile of formula:

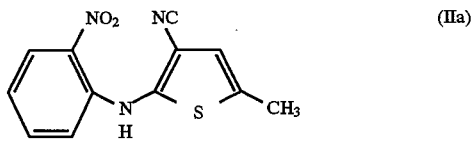

which can be simultaneously reduced and ring-closed to the amidine of formula (II) employing, for example, stannous chloride and hydrogen chloride in aqueous ethanol or, alternatively by reduction with hydrogen and palladium/carbon or ammonium polysulphide followed by acid-catalysed ring closure. The intermediate of formula (IIa) may be isolated using ammonium chloride (NH₄Cl) or ammonium acetate (NH₄OAc).

When Q is hydroxyl, reaction (a) is preferably carried out in the presence of titanium tetrachloride which has the ability to react with the N-methylpiperazine to form a metal amine complex. Other metal chlorides such as those of zirconium, hafnium or vanadium may also be employed. The reaction can be carried out in the presence of an acid binding agent such as a tertiary amine, for example, triethylamine.

Alternatively, the reaction can be carried out using excess of N-methylpiperazine to act as an acid-binding agent. A suitable organic solvent such as toluene or chlorobenzene can be used as a reaction medium, although the use of anisole is particularly desirable, at least as a co-solvent, in view of its ability to form a soluble complex with TiCl₄.

If desired, elevated temperatures, for example up to 200° C., can be used to hasten the reaction and a preferred temperature range for carrying out the reaction is from 80° C. to 120° C.

The intermediate amide of formula (II) (Q is —OH) can be prepared from the corresponding amidine (Q is —NH₂) by alkaline hydrolysis, or can be derived from compounds of formula

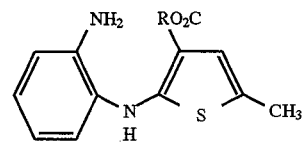

in which R is an ester group, preferably $C_{1-4}$ alkyl, by ring closure employing, for example, sodium methylsulphinyl methanide in a suitable solvent such as dimethylsulphoxide. Alternatively, the amide can be prepared by ring closure of an amino-acid, employing for example dicyclohexylcarbodiimide (DCC) in a suitable solvent such as tetrahydrofuran. The amino-acid can be obtained for example from the above esters by basic hydrolysis using for example sodium hydroxide in ethanol.

Thioamides of formula (II) (Q is —SH), iminothio-ethers, iminoethers or iminohalides, or other derivatives containing active Q radicals as specified above, tend to be more reactive towards N-methylpiperazine and can usually be reacted without the necessity for the presence of TiCl₄, but otherwise employing the same conditions of temperature and solvent.

The thioamide of formula (II) (Q is —SH) can be prepared by treating a solution of the corresponding amide in an anhydrous basic solvent, such as pyridine, with phosphorous pentasulphide. Similarly, the amide can be converted to the iminothioether, iminoether or iminohalide, or other derivatives containing active Q radicals, by treatment with conventional reagents such as for example in the case of the iminochloride, phosphorous pentachloride.

The intermediate compounds of formula (II) in which Q is a radical capable of being split off, particularly those in which Q is —NH₂, —OH or —SH and when Q is —NH₂ salts thereof, are novel compounds, and form a further aspect of the present invention.

With regard to reaction (b) above, the compound of formula (III) may be ring-closed by employing, for example, titanium tetrachloride as catalyst and anisole as solvent, and the reaction is preferably carried out at a temperature of 100° C. to 250° C., for example from 150° C. to 200° C.

The intermediate compound of formula (III) is preferably prepared in situ without isolation by reacting a compound of formula

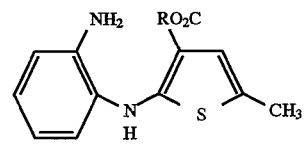

in which R is an ester group, preferably $C_{1-4}$ alkyl, with N-methylpiperazine, by heating to a temperature of between 30° C. and 120° C., for example about 100° C., in a suitable solvent such as for example anisole, and employing TiCl₄ as catalyst.

The compound of formula (IV) can be prepared from the corresponding nitro compound of formula

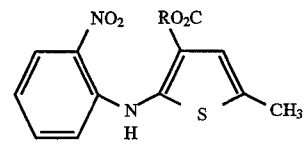

Such compounds of formula (V) in which R is an ester group, such as for example $C_{1-4}$ alkyl, are novel and form a further aspect of the invention.

If convenient this nitro compound can be converted to the amine of formula (IV) without isolation, before reaction with N-methylpiperazine. Intermediate compounds of formula (V) can be made by condensation of a thiophene of formula

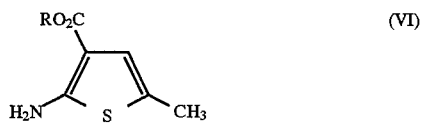

with an ortho-halonitrobenzene, preferably ortho fluoro- or chloro- nitrobenzene, in the presence of a base, for example, (a) sodium hydride in a solvent such as for example tetrahydrofuran and at a temperature of from −20° C. to 30° C., or (b) anhydrous potassium carbonate or lithium hydroxide in a solvent such as dimethylsulphoxide at a temperature of from 90° C. to 120° C. The compound of formula (V) is converted to that of formula (IV) by reduction, for example catalytically, employing hydrogen and palladium/carbon, or chemically, employing stannous chloride and hydrogen chloride in aqueous ethanol, or ammonium polysulphide, or zinc in aqueous ammonium chloride.

It will be appreciated that the compound of formula (I) may be isolated per se or may be converted to an acid addition salt using conventional methods.

As mentioned above, 2-methyl-4-(4-methyl-1-piperazinyl)-10H-thieno[2,3-b][1,5]benzodiazepine has useful central nervous system activity. This activity has been demonstrated in models using well-established procedures. For example, the compound has been assessed in a number of standard behavioral tests predictive of antipsychotic activity. It antagonized apomorphine-induced climbing behavioral and hypothermia in mice (Moore, N. A. et al. Psychopharmacology 94 (2), 263–266 (1988), and 96, 539 (1988)) at doses of less than 10 mg/kg. The compound also inhibited a conditioned avoidance response in rats ($ED_{50}$ 4–7 mg/kg), but unlike standard compounds, it induced catalepsy only at much higher doses ($ED_{50}$ 39.4 mg/kg). This separation between the doses required to block a conditioned avoidance response and to induce catalepsy indicates that the compound is less likely to induce extrapyramidal side effects in the clinic.

The compound 2-methyl-4-(4-methyl-1-piperazinyl)-10H-thieno[2,3-b][1,5]benzodiazepine was also active at doses of less than 10 mg/kg in a test based on the apomorphine-induced climbing test referred to above, which measured the ability of the compound to prevent the disruption of climbing response produced by 24 hour pretreatment with N-ethoxycarbonyl-2-ethoxy-1,2-dihydroquinoline (EEDQ), a dopamine receptor inactivating agent (Meller et al. Central D1 dopamine receptors, Plenum Press, 1988). This test shows that the compound possesses activity at both the D-1 and D-2 receptors.

The 2-methyl-4-(4-methyl-1-piperazinyl)-10H-thieno[2,3-b][1,5]benzodiazepine compound was active in the multiple conflict schedule at doses of less than 5 mg/kg. Moore, Nicholas A. et al., *The Journal of Pharmacology and Experimental Therapeutics*, 545–551, 262:2 (1992). The test measures characteristic changes in rates of responding associated with anxiolytic agents. The conflict procedure results are indicative of favorable anxiolytic activity.

The conflict procedure used was based on the method of Geller and Seifter, *Psychopharmacologia* 1: 482–492, (1960). Rats were trained on a multiple schedule consisting of three components. Individual components were as follows: 1) for 9 minutes, lever pressing was reinforced on a variable interval 30 second schedule (VI 30, reward). This period was signaled by illumination of the houselight alone. 2) During the following 3-minute period, lever presses were recorded but had no programmed consequence (time-out). 3) Lever pressing was reinforced according to a fixed ratio 10 second food presentation (FR10) for 3 minutes; however, each reinforced response was accompanied by an electric current (0.5 mA) being applied to the grid floor for 500 msec (conflict). This component was signaled by illumination of the houselight and three cue lights on the front panel. This sequence of three components (reward/time-out/conflict) was presented twice in the same order during the daily 30 minute session. Animals were given extensive training on this schedule until the following criteria had been satisfied: 1) rates of responding during the individual VI30 components did not differ by more than 10%; 2) rates of responding during time-out and conflict were less than 10% of the rate during the VI component; and 3) the above criteria were satisfied for a period of five days.

After the training procedure, drug testing was initiated. During this period, the animals were dosed orally with either test compounds or vehicle in a randomized order 60 minutes before testing. At least two drug-free training days occurred between test sessions. This test indicates that the compound has anxiolytic properties which are not observed with typical antipsychotic agents. Spealman et al., *J. Pharmacol. Exp. Ther.*, 212:435–440, 1980.

In addition, 2-methyl-4-(4-methyl-1-piperazinyl)-10H-thieno[2,3-b][1,5]benzodiazepine has been found to have a favorable profile of activity in a number of in vitro binding assays, designed to measure the degree of binding to neural receptors.

In keeping with the observations made in the behavioral tests, the compound is active at both the dopamine D-1 and D-2 receptors as indicated by an $IC_{50}$ of less than 1 μM in the $^3$H-SCH23390 (Billard, W. et al. Life Sciences 35 1885 (1984)) and the 3H-spiperone (Seeman, P. et al. Nature 261 717 (1976)) binding assays respectively.

The compound has an $IC_{50}$ of less than 1 μM in the $^3$H-QNB binding assay described by Yamamura, HI and Snyder, SH in Proc.Nat.Acad. Sci. USA 71 1725 (1974) indicating that it has antimuscarinic-anticholinergic activity. In addition, the compound shows its greatest activity at the 5-HT-2 receptor in that it displaces H-spiperone from binding sites in the rat frontal cortex (Peroutka, S. J. and Snyder, S. H. Mol. Pharmacol. 16 687 (1979)) at low nanomolar concentrations. The compound is also active at the 5-HT-1C receptor.

This profile of activity in in vitro receptor binding assays, like that observed in the behavioral tests, would indicate that the compound is effective in the treatment of psychotic conditions but is less likely to induce extrapyramidal side-effects. The behavioral tests and in vitro binding assays indicate that the compound is an effective anxiolytic agent and is useful for the treatment of other pathologic psychological conditions.

The 2-methyl-4-(4-methyl-1-piperazinyl)-10H-thieno[2,3-b][1,5]benzodiazepine compound is effective over a wide dosage range, the actual dose administered being dependent on the condition being treated. For example; in the treatment of adult humans, dosages of from 0.25 to 30 mg, preferably from 1 to 20 mg, per day may be used. A once a day dosage is normally sufficient, although divided doses may be administered. For treatment of psychotic disorders a dose range of from 1 to 20 mg, preferably 2.5 to 15 mg per day is suitable, whereas for mild anxiety states a lower dosage range, such as from 0.25 to 5 mg, preferably 1 to 5 mg, may be more appropriate. In choosing a suitable regimen for patients suffering from psychotic illness it may frequently be necessary to begin with a dosage of from 1 to 20 mg per day and when the illness is under control to reduce to a dosage as low as 1 mg per day. In studies using radiolabelled compound of the invention, residues have been detected in the saliva and thus the compound can potentially be monitored in patients to assess compliance.

The 2-methyl-4-(4-methyl-1-piperazinyl)-10H-thieno[2,3-b][1,5]benzodiazepine compound will normally be administered orally or by injection and, for this purpose, it is usually employed in the form of a pharmaceutical composition.

Accordingly the invention includes a pharmaceutical composition comprising as active ingredient a compound of formula (I) or a pharmaceutically acceptable acid addition salt thereof, associated with a pharmaceutically acceptable carrier. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions may be formulated as tablets, granules, capsules, depot formulation, injection solutions for parenteral use, gel or suspension for transdermal delivery, suspensions or elixirs for oral use or suppositories. Preferably the compositions are formulated in a dosage unit form, each dosage containing from 0.25 to 30 mg, more usually 1 to 20 mg, of the active ingredient. A preferred formulation of the invention is a capsule or tablet comprising 0.25 to 30 mg or 1 to 20 mg of active ingredient together with a pharmaceutically acceptable carrier therefor. A more preferred formulation is a tablet comprising 1, 2.5, 5, 7.5 or 10 mg of active ingredient together with a pharmaceutically acceptable carrier therefor. A further preferred formulation is an injection which in unit dosage form comprises 0.25 to 30 mg or 1 to 20 mg of active ingredient together with a pharmaceutically acceptable diluent therefor. A type of injection formulation that is especially desirable is a sustained release formulation for intramuscular injection. Another preferred formulation is a granule formulation. The granule formulation may serve as a reconstitutable solid.

The invention is illustrated by the following Examples.

EXAMPLE 1

1. 2-Amino-5-methylthiophene-3-carbonitrile

A mixture of sulfur (217.8 g, 6.79 mol), propional-dehyde (472.5 g, 587 mL, 8.13 mol) and dimethylformamide (1350 m) was placed in a 5 liter flange-necked flask fitted with air stirrer, air condenser, long reach thermometer and dropping funnel. Triethylamine (576 mL, 4.13 mol) was added dropwise over 30 minutes to the cooled stirred reaction mixture whilst maintaining the pot temperature between 5°–10° C. with an ice-bath. After addition was complete the pot was allowed to warm up to 18° C. over 50 minutes, keeping the mixture well stirred. Then a solution of malononitrile (450 g, 6.8 mol) in dimethylformamide (900 mL) was added dropwise over 70 minutes keeping the pot temperature around 20° C. throughout the addition. After addition was complete the mixture was stirred at 15°–20° C. for a further 45 minutes then sampled for TLC. The mixture was then poured onto ice (4 liters)/water (8 liters) with stirring and this caused the required product to precipitate. After 10 minutes the stirrer was switched off and the solid allowed to settle. The aqueous liquor was decanted away and the solid isolated by filtration. The isolated solid was well washed with water (deionized, 4 liters), then dried over night in vacuo at 70°–75° C. to give the title compound (585 g), m.p. 100° C.

2. 2-(2-Nitroanilino)-5-methylthiophene-3-carbonitrile

To a stirred slurry of sodium hydride (14.4 g, 50% dispersion in oil, 0.3 mol) in dry tetrahydrofuran (50 mL) under nitrogen was added, dropwise, a solution of 2-fluoronitrobenzene (28.2 g, 0.2 mol) and 2-amino-5-methylthiophene-3-carbonitrile (27.6 g, 0.2 mol) in dry tetrahydrofuran (250 mL). The mixture was stirred at 25° C. for 24 hours, poured onto cracked ice and extracted into dichloromethane (3×500 mL). The combined extracts were washed with 2N hydrochloric acid (2×200 mL), water (2×200 mL), dried over magnesium sulfate and the solvent removed under reduced pressure. The residue was crystallized from ethanol to give the title compound, (35.2 g), m.p. 99°–102° C.

3. 4-Amino-2-methyl-10H-thieno[2,3-b][1,5]benzodiazepine, hydrochloride

To a stirred slurry of 2-(2-nitroanilino)-5-methylthiophene-3-carbonitrile (3 g, 0.011 mol) in ethanol (35 mL) at 50° C. was added, over 10 minutes, a solution of anhydrous stannous chloride (6.95 g, 0.037 mol) in hydrochloric acid (26 mL, 5M). The mixture was stirred under reflux for 1 hour, concentrated under reduced pressure and allowed to crystallize over night at 5° C. The salt was filtered, washed with a small amount of water, dried (4.3 g) m.p. >250° C., and used without further purification in the next stage.

4. 2-methyl-4-(4-methyl-1-piperazinyl)-10H-thieno-[2,3-b][1,5]benzodiazepine

Crude 4-amino-2-methyl-10H-thieno[2,3-b][1,5]benzodiazepine, hydrochloride (4.3 g) was refluxed in a mixture of N-methylpiperazine (15 mL), dimethylsulphoxide (20 mL) and toluene (20 mL) under a nitrogen atmosphere for 20 hours. The mixture was cooled to ca. 50° C., water (20 mL) added, and the product allowed to crystallize at 5° C. over night. The product was filtered and crystallized from acetonitrile (30 mL) to give the title compound (1.65 g) m.p. 195° C.

The structure of the compound was confirmed spectroscopically:

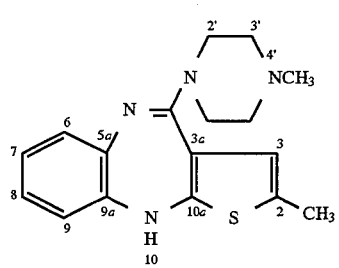

$^1$H NMR (CDCl$_3$): δ 2.30 (3H, s, 4'-CH$_3$), 2.28 (3H, s, 2-CH$_3$), 2.45 (4H, m, 3'-CH$_2$) 3.49 (4H, m, 2'-CH$_2$), 5.00 (H, broad s, 10-NH), 6.23 (H, broad s, 3-CH), 6-35-7-10 (4H, m, 6,7,8,9-H).

$^3$C NMR (CDCl$_3$): δ 128.5 (s, C-2), 127.8 (d, C-3), 119.1 (s, C-3a), 157.4 (s, C-4) 140.8 (s, C-5a), 123.4, 122.6, 124.1 (d, C-6,7,8), 118.8 (d, C-9), 142.5 (s, C-9a), 151.8 (s, C-10a), 46.5 (t, 2'-C), 54.8 (t, 3'-C) 45.9 (q, -4'-C), 15.2 (q, 2-Me).

Mass spectra shows an M+ of 312 and major fragment ions of m/z 255, 242, 229 and 213.

EXAMPLE 2

1. Methyl 2-amino-5-methylthiophene-3-carboxylate

To a stirred mixture of methyl cyanoacetate (3.9 g, 0.04 mol), sulfur (1.26 g, 0.04 mol) and triethylamine (3.2 mL, 002 mol) in dry methylformamide (12 mL) under a nitrogen atmosphere at 45° C. was added, dropwise, a solution of freshly distilled propionaldehyde (2.5 g, 0.043 mol) in dry dimethylformamide (2 mL), keeping the temperature at 45°–47° C. The mixture was stirred at 45° C. for 1.5 hours, then partitioned between water and ethyl acetate. The organic extract was washed with water, dried and evaporated. The title compound was purified by chromatography on neutral alumina, eluting with chloroform-hexane (4.8 g)

2. Methyl 2-(2-nitroanilino)-5-methylthiophene-3-carboxylate

To a stirred suspension of sodium hydride (2 g) in dry tetrahydrofuran (25 mL) under a nitrogen atmosphere was added a solution of methyl 2-amino-5-methylthiophene-3-carboxy-late (4.8 g, 0.028 mol) and 2fluoronitrobenzene (4.0 g, 0.025 mol) in dry tetrahydrofuran (30 mL). The mixture was stirred at 25° C. for 20 hours, poured onto ice and partitioned between 2N hydrochloric acid and ethyl acetate. The organic extracts were dried over magnesium sulfate, the solvent was evaporated under reduced pressure and the title compound purified by chromatography on silica gel, eluted with toluene, and crystallized from ethanol (4.1 g).

3. 2-Methyl-4-(4-methyl-1-piperazinyl)-10H-thieno[2,3-b][1,5]benzodiazepine Methyl 2-(2-nitroanilino)-5-methylthiophene-3-carboxy-late (3.7 g, 0.0013 mol) was hydrogenated in a Parr apparatus at 60 psi in ethanol-ethyl acetate (2:1, 150 mL) with palladium on charcoal catalyst (10%, 200 mg). After removal of catalyst and solvent the crude diamino-ester was dissolved in a mixture of N-methylpiperazine (21 mL) and anisole (55 mL). To this solution, under a nitrogen atmosphere was added, with stirring, a solution of titanium tetrachloride (3.45 mL) in anisole (15 mL). The mixture was stirred at 100° C. for 1 hour, then under reflux for 48 hours to effect ring closure of 1-{[2-(2-amino anilino)-5-methylthiophen-3-yl]carbonyl}-4-methylpiperazine.

After allowing to cool to 80° C. a mixture of 30% ammonia solution (10 mL) and isopropanol (10 mL) was cautiously added, followed by ethyl acetate (25 mL). The inorganic precipitate was removed by filtration and the filtrate washed with water (3×25 mL), dried with magnesium sulfate and the solvent removed under reduced pressure. The product was purified by chromatography on Florisil, eluted with ethyl acetate and finally crystallized from acetonitrile (40 mL) to give the title compound (2.32 g), identical with that described above.

EXAMPLE 3

A pulvule formulation is prepared by blending the active with silicone starch, and filling it into hard gelatin capsules.

|  | Per 300 mg capsule |
| --- | --- |
| Compound of the invention | 5.0 mg |
| Silicone | 2.9 mg |
| Starch flowable | 292.1 mg |

EXAMPLE 4

A tablet formulation is made by granulating the active with appropriate diluent, lubricant, disintegrant and binder and compressing

| Compound of the invention | 5.0 mg |
| --- | --- |
| Magnesium stearate | 0.9 mg |
| Microcrystalline cellulose | 75.0 mg |
| Povidone | 15.0 mg |
| Starch, directly compressible | 204.1 mg |

EXAMPLE 5

An aqueous injection of active is prepared as a freeze-dried plug, for reconstitution in a suitable, sterile 25 diluent before use (to a total volume of 10 ml).

Compound of the invention Mannitol N Hydrochloric acid and/or N sodium hydroxide to adjust pH to5–5.5,

| Compound of the invention | 20.0 mg |
| --- | --- |
| Mannitol | 20.0 mg |
| N Hydrochloric acid and/or N sodium hydroxide to adjust pH to 5–5.5. | |

EXAMPLE 6

A controlled release injection for intramuscular injection is formed from a sterile suspension of micronised active in an oleaginous vehicle.

| Compound of the invention | 65.0 mg |
| --- | --- |
| Aluminium stearate | 0.04 mg |
| Sesame oil | 2 ml |

EXAMPLE 7

A formulation is prepared by blending the active with silicone starch and starch, and filling it into hard gelatine capsules.

|  | Per 290 mg capsule |
| --- | --- |
| Compound of the invention | 2.5 mg |
| Starch flowable with 0.96% silicone 220 | 217.5 mg |
| Starch flowable | 70.0 mg |

We claim:

1. A method of treating a patient suffering from or susceptible to psychosis selected from the group consisting of Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; and Major Depression, Single Episode, with Psychotic Features; comprising administering to a patient in need thereof an effective amount of 2-methyl-4-(4-methyl-1-piperazinyl)-10H-thieno-[2,3-b][1,5]benzodiazepine, acid addition salt thereof.

2. A method of claim 1 for treating a patient suffering from or susceptible to a condition selected from the group consisting of Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; and Major Depression, Single Episode, with Psychotic Features.

3. A method of claim 2 for treating a patient suffering from or susceptible to a condition selected from the group consisting of Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; and Schizoaffective Disorder.

4. A method of claim 1 wherein the effective amount is from 1 to 20 mg per day of 2-methyl-4-(4- methyl-1-piperazinyl)-10H-thieno-[2,3-b][1,5]benzodiazepine, or an acid addition salt thereof.

5. A method of treating a patient suffering from or susceptible to an anxiety disorder selected from the group consisting of Psychoactive Substance Anxiety Disorder; Organic Anxiety Disorder; Obsessive Compulsive Disorder; Post-traumatic Stress Disorder; Generalized Anxiety Disorder; and Anxiety Disorder NOS; comprising administering to a patient in need thereof an effective amount of 2-methyl-4-(4-methyl-1-piperazinyl)-10H-thieno[2,3-b][1,5]benzodiazepine, or an acid addition salt thereof.

6. A method of claim 5 wherein the effective amount is from 1 to 20 mg per day of 2-methyl-4-(4- methyl-1-piperazinyl)-10H-thieno-[2,3-b][1,5]benzodiazepine, or an acid addition salt thereof.

7. A method of claim 5 for treating an animal, including a human, suffering from or susceptible to an anxiety disorder selected from the group consisting of Organic Anxiety Disorder; Obsessive Compulsive Disorder; Post-traumatic Stress Disorder; Generalized Anxiety Disorder; and Anxiety Disorder NOS.

8. A method of treating a patient suffering from or susceptible to a pathologic psychological condition wherein delusions, hallucinations, disorganized behavior, or anxiety are a consistent manifestation of the pathologic condition, comprising administering to a patient in need thereof an effective amount of 2-methyl-4-(4-methyl-1-piperazinyl)-10H-thieno[2,3-b][1,5]benzodiazepine, or an acid addition salt thereof.

9. A method of claim 8 wherein delusions, hallucinations, or disorganized behavior are a consistent manifestation of the pathologic condition.

10. A method of claim 8 wherein the effective amount is from 1 to 20 mg per day of 2-methyl-4-(4-methyl-1-piperazinyl)-10H-thieno-[2,3b][1,5]benzodiazepine, or an acid addition salt thereof.

* * * * *